United States Patent
Rehmeyer et al.

[11] Patent Number: 6,007,771
[45] Date of Patent: *Dec. 28, 1999

[54] METHOD OF CLEANING NON-PERMEABLE CONTACT LENS

[76] Inventors: Theodore H. Rehmeyer, 3411 Scarborough Dr., Winston-Salem, N.C. 27106; James R. Shultz, 1267 Wiltshire Rd., York, Pa. 17403

[ * ] Notice: This patent is subject to a terminal disclaimer.

[21] Appl. No.: 08/896,987

[22] Filed: Jul. 18, 1997

[51] Int. Cl.⁶ ........................................................ A61L 2/02
[52] U.S. Cl. .............................. 422/23; 422/22; 422/300; 134/901; 206/5.1; 204/551; 204/600
[58] Field of Search ................................. 422/22, 23, 300; 134/901; 206/5.1, 6; 204/551, 600; 205/701, 769

[56] References Cited

U.S. PATENT DOCUMENTS

| | | | |
|---|---|---|---|
| 5,368,708 | 11/1994 | Pankow | 422/24 X |
| 5,439,572 | 8/1995 | Pankow | 134/901 X |
| 5,657,506 | 8/1997 | Pankow | 15/104.92 |
| 5,783,147 | 7/1998 | Reymeyer et al. | 422/22 |

*Primary Examiner*—Elizabeth McKane

[57] ABSTRACT

Apparatus and methods for holding and cleaning non-permeable contact lenses which includes the application of an electromagnetic field about the contact lenses which are held in a cavity containing a conductive solution and an adsorbent membrane to capture the contaminants being removed from the lenses. Proteins, lipoproteins and other contaminants adhere to the surface of non-permeable lenses. An adsorbent is positioned between the lens and an electric current source so that current flows from the current source through the adsorbent and over the surface of the contact lens so that contaminants on the lens are loosened and migrate to the adsorbent to which they adhere, thus permitting effective removal from the solution. A lens holding device formed by a novel method is used with the cleaning apparatus and includes joined body portion sections foldable upon each other along a fold line, the sections having openings therein which align with each other when the sections are folded to form, along with closing seals, holding compartments. Depending upon current levels and the time period involved, contaminant removal can exceed 90% with the use of less than 0.25 watt of energy.

23 Claims, 2 Drawing Sheets

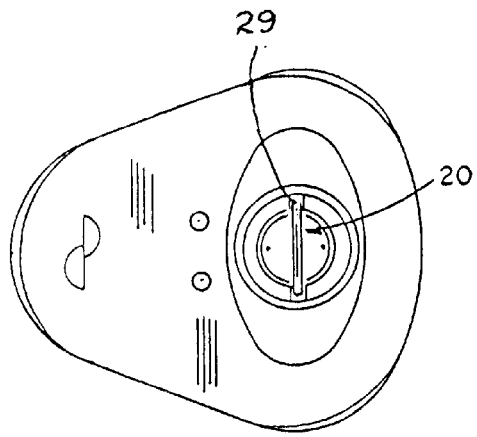
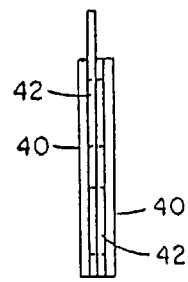
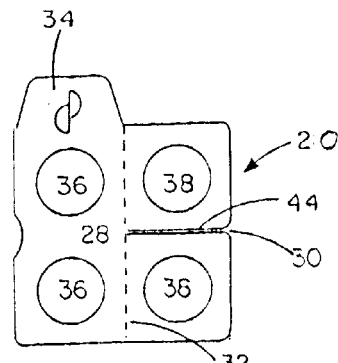
FIG. 1   FIG. 7   FIG. 6
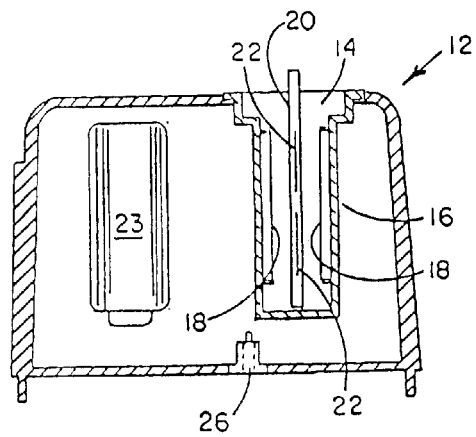
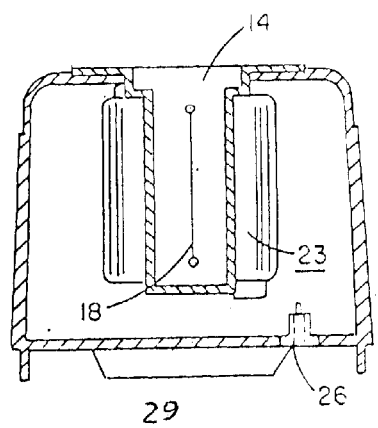
FIG. 2   FIG. 3
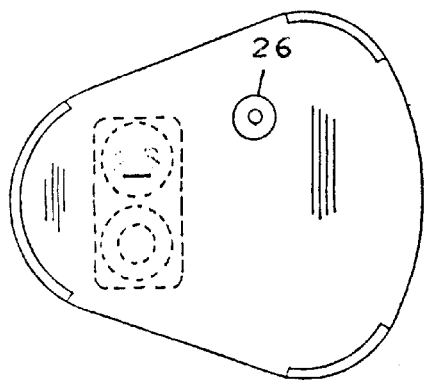
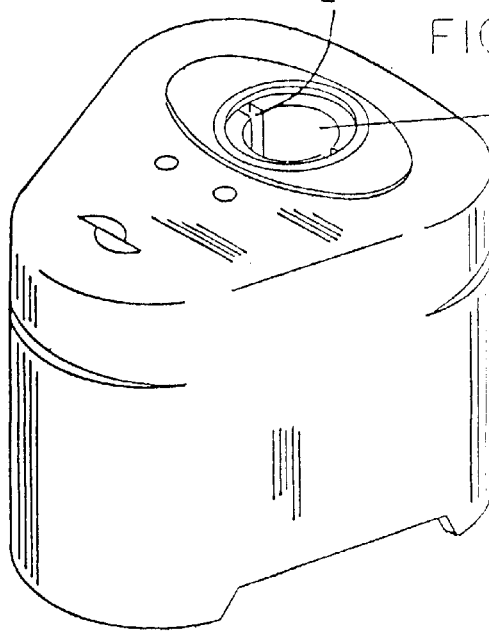
FIG. 4   FIG. 5

METHOD OF CLEANING NON-PERMEABLE CONTACT LENS

FIELD OF THE INVENTION

The present invention relates generally to the cleaning of contact lenses and more particularly to removing contaminants from the surface of non-permeable contact lenses through the use of a power source and an adsorbent.

BACKGROUND OF THE INVENTION

The most disagreeable problem to wearer comfort and visual acuity of contact lenses is the presence of contaminants on the surface of the lens. Those contaminants, for the most part, are proteins, lipoproteins, and other contaminants (hereinafter referred to as "contaminants") produced by the eye, tear duct, and eyelid for lubrication and protection of delicate optic tissues. Contaminants will collect on the surfaces of non-permeable lenses to form small protrusions which rub against the sensitive ocular tissues to promote inflammation and discomfort.

There are a number of known methods for removing contaminants from a contact lens surface including the use of a mild detergent to wash the lens surface and the use of a proteolytic enzyme which digests the protein molecules. However, these methods are only partially effective and may, in some cases, damage the lens.

Other methods of removing protein from contact lens are shown in a number of patent references. For example, U.S. Pat. No. 4,921,544 (Cowle et al.) discloses a method wherein the contact lens is placed in an electrophoretic solution within a container, an electric field is applied to the solution through two electrodes in the solution, and the charged protein molecules attached to the lens migrate to the oppositely charged electrode. However, in this method, migration eventually reaches an equilibrium at which point it becomes very difficult to remove additional proteins from the solution. U.S. Pat. No. 4,872,965 (Pankow) offers a method wherein electrodes are immersed in solution baths external to the lens and current is provided to the lens by a transmission means which rests on the lens surface. From this point, the contaminants are removed from either the lens surface or from the electrochemical transmission means by an additional wiping step. This method was particularly adaptable to clean lenses made from hydrophilic materials which absorb large proportions of water within the lattice they create.

U.S. Pat. No. 5,292,372 (Swaisgood et al.) is directed to a method of removing contaminants from permeable contact lenses (an adsorbent is used with the contact lens so the adsorbent is disposed between the lens and an electric current source). The immersed lens, adsorbent and current source are positioned in a container which holds an aqueous saline solution, and an electric current is applied from the source through the adsorbent and through the lens so that contaminants removed from the lens migrate to the adsorbent.

SUMMARY OF THE INVENTION

The present invention includes an apparatus for removing contaminants from the surface of non-permeable contact lens which has a housing in which resides a cleaning well. Electrodes and adsorbent material are positioned near contact lens held by a holding device and a power source. A quantity of cleaning solution is placed in the cleaning well immersing the electrodes, contact lens and adsorbent material so that upon actuation by a control device, current will flow from the power source through the electrodes, the cleaning solution, the adsorbent material and over the surface of the contact lens and back to the power source so that contaminants on the contact lens migrate through the current field and are captured by the adsorbent.

The use of an adsorbent material, as opposed to an absorbent material, is of particular importance in the present inventive concept. Absorption involves the penetration of one substance into the inner structure of another whereas in adsorption, one substance is attracted to and held on the surface of another. An adsorbent is a substance which attracts the atoms, ions, or molecules of a gas or liquid to its surface. Finely divided or microporous materials presenting a large area of active surface are strong adsorbents and are used in removing colors, odors, water vapor and the like. In the present inventive concept, the contaminants on the contact lens are moved through the electromagnetic field and captured on the surface of the adsorbent material.

A method included in the present invention is for cleaning non-permeable contact lenses through which current and proteins cannot flow. In the method, very low current is used to facilitate the flow of contaminants from the surface of the lens and onto an adsorbent membrane. No current flow through the lens takes place because non-permeable lenses are effective insulators and do not permit current flow therethrough. In the method, the contact lens, an adsorbent and an electric current are configured so that current passes through the solution, over the surface of the lens and through the adsorbent which has an affinity for contaminants. The contaminants attached to the lens surface migrate to the adsorbent upon the application of current. The method is effectively practiced with the use of a voltage source of less than 28 volts and a current level of from 0.1 to 50 milliamperes. The process is highly efficient in that it removes more than 90% of the contaminants and has a power requirement of less than 0.25 watt.

The lens holding device used with the lens cleaning apparatus of the present invention includes a body portion having first and second body portion sections which are integrally joined and foldable upon each other along a fold line. At least two openings are formed in each of the body portion sections, the openings in the first section positioned to align with the openings of the second section and form at least two cylindrical openings to hold the lens. A closing film covers and closes each of the outside surface openings in the first and second body portion sections so that the closing film and the openings in each body portion section formed closed lens holding compartments to maintain the lens in a relatively fixed relationship with each other and with the electrodes when the first and second body portion sections are folded upon each other along the fold line.

The contact lens holding device is formed by advancing a plastic material along a preselected path of travel from a supply roll, advancing an adhesive film along the same path of travel from another supply roll against the plastic material, and pressure bonding the adhesive film to the plastic material. Circular openings are formed in the bonded plastic material and adhesive film, and a protein binding membrane from a supply roll is moved along the path of travel and against the adhesive film to adhere the protein binding membrane to the plastic material and ultimately form the lens holding compartments therein. The plastic material, bonded adhesive film and protein binding membrane are thereafter cut into discrete lengths to provide a plurality of contact lens holding devices.

DRAWINGS

FIG. 1 is a top plan view of the lens cleaning apparatus in which is positioned the lens holding device;

FIG. 2 is a side elevational, sectional view of the lens cleaning apparatus and the lens holding device shown in FIG. 1;

FIG. 3 is an end elevational, sectional view of the contact lens cleaning apparatus and the lens holding device shown in FIGS. 1 and 2;

FIG. 4 is a bottom sectional view of the contact lens cleaning apparatus and lens holding device shown in FIGS. 1, 2 and 3;

FIG. 5 is a perspective view of the contact lens cleaning device shown in FIGS. 1, 2, 3 and 4;

FIG. 6 is an opened view of the lens holding device forming a part of the present invention;

FIG. 7 is an end elevational folded and closed view of the lens holding device comprising a part of the present invention.

DETAILED DESCRIPTION OF THE INVENTION

Figure 8:
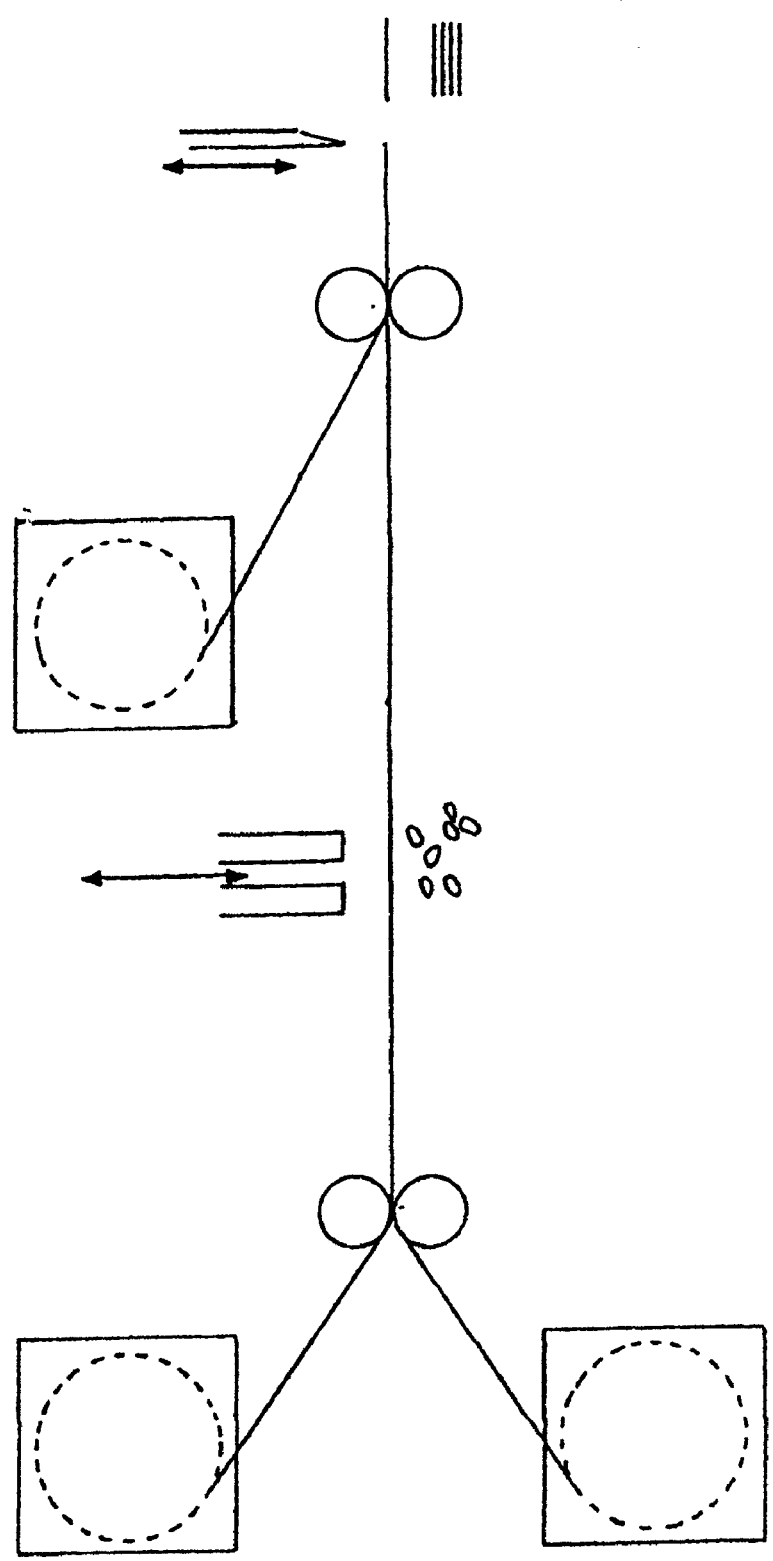
FIG. 8 is a block schematic diagram of the steps included in the process forming the lens holding device.

The present invention is directed to a method of removing contaminants from the surface of contact lenses. The method comprises positioning the contact lens and an adsorbent so that the adsorbent is disposed between the contact lens and an electric current source, immersing the contact lens, adsorbent and current source in a container which holds an aqueous saline solution, and applying an electric current from the source through the adsorbent and around the lens so that the contaminants on the lens surface migrate from that surface to the adsorbent.

This method relies on the principles of electroblotting, a process wherein electric current is applied to a substrate which contains ionic material. Individual charged molecules are attracted by and migrate to an electrode or other charged device. In the present invention, the materials removed by the current are contaminants retained on contact lenses which, upon the application of current, migrate toward the electrically charged device. The contaminants are then captured by an adsorbent having an affinity therefor which retains the contaminants. When the application of current ceases, the contaminant-laden adsorbent is removed. The cleaned lens is ready for reinsertion by the wearer.

The method of the present invention is suitable for use with any contact lens that is not capable of passing an electric current while immersed in saline solution. It is preferred that the lens be made of plastic materials with pore sizes too small for the penetration of proteins and other contaminants into the interstices of the lens. Such lenses are sold under the names and are made of materials as follows:

| Brand Name | Material Description |
| --- | --- |
| Boston II and IV | Silicone Acrylate |
| Boston Equalenes, R.X.D. 7 ES | Fluosilicone Acrylate |
| Fluorex 300, 500, 700 | Fluorosilicate Acrylate |
| Fluoroperm, Optacryl | Fluorosilicone Acrylate |
| Novalens | Silicone Acrylate |
| Novalens | Strysilicone |
| O->Perm F60 | Fluoro-Sioloxane Acrylate |
| SF-P | Fluoro-Siloxane Acrylate |
| SGP, SGPII | Siloxane Acrylate |
| SGP 3 | Fluoro-Siloxane Acrylate |
| Trans-Aire | Silicone Acrylate |
| The Alberta Lens "S" and (45) silicone | Polysulfone-fluoro-Acrylate |

The choice of adsorbent used to form the lens-adsorbent complex is not critical; any adsorbent to which contaminants on the lens will adhere is suitable. Exemplary adsorbents include polymer membranes, such as PVDF, and cellulosic papers. It is preferred that the material comprising the adsorbent include a free chemical substituent which has a high affinity for protein, such as an amino, nitro, or carboxyl group.

Although the adsorbent can be of any shape which permits it to be disposed between the electrically charged device and the lens, the lens holder forming a part of the present invention has been found particularly effective in positioning the lens against or in close proximity to the adsorbent so that any contaminants migrating from the surface of the lens will immediately be trapped in the adsorbent and will not remain in solution where potentially they could return to the lens surface. A preferred protein binding membrane is made by Gelman Sciences, Inc. of Ann Arbor, Mich.

The choice of saline solution is not critical; any known saline solution for cleaning or soaking of contact lenses is suitable. Exemplary saline solutions can include as part of the total solution, boric acid, sodium borate, sodium chloride, ascorbic acid, and edetate disodium (EDTA). The pH of the saline solution should be such that it does not coincide with the isoelectric point of the protein contaminants; otherwise, the contaminants would have no electrical charge and thus, would not migrate from the lens surface. It is also preferred that the saline solution be buffered to provide a constant pH solution. This ensures that such migrating proteins will maintain that charge during migration and therefore migrate reproducibly. The concentration of the solution is not critical; however, a dilute saline solution is preferred for rapid migration of contaminants.

Referring now to the drawings and particularly to FIG. 2, a lens holding device shown generally as 12 has an opening 14 substantially circular in configuration and adapted to receive a cylindrical well 16 which contains electrodes 18, a lens holder 20 and lens 22 within the lens holder as shown. Well 16 also holds a quantity of saline solution that surrounds electrodes 18, lens holder 20 and lens 22 carried thereby. A power source can be a battery 23 or a converter from ordinary household current source through an AC to DC, adapter and jack 26 as shown. A slotted opening 29 (FIG. 1) is formed in the top of well 16, and the adjacent edges of opening 29 are beveled to provide room for two fingers of the user to insert lens holder 20 with lens 22 and thereafter remove it when the lens have been cleaned.

The application of an electric current to the solution containing lens holder 20 with lens 22 can be done in many ways so that the current passes through the membranes of lens holder 20 and around the surface of lens 22 held within the membranes. The current is supplied by electrodes 18 immersed in the saline solution itself, but those skilled in this art will appreciate that any means of supplying current around the lens which causes the contaminants thereon to ionize and migrate to a charged device is suitable. When immersed electrodes 18 are used, they are preferably placed so that current flows uniformly over as much of the surface area of lens 22 as possible. In the preferred orientation of FIG. 2, electrodes 18 are placed on opposite sides of lens 22 so that current flowing between the electrodes flows substantially parallel to an axis extending through the diametric center of the lens.

Lens holding device 20 (FIG. 6) is formed a body portion having a first body portion section 28 and a second body portion section 30 as shown in FIG. 6. Sections 28, 30 are integrally joined and foldable upon each other along a fold line 32. A handling tab 34 joins first body portion section 28 and is preferably integral therewith and functions cooperatively with the beveled edges of slotted opening 28 for ease in inserting device 20 in well 16. Device 20 in FIG. 6 is constructed to clean one pair of contact lens simultaneously and therefore has two openings 36 in section 28 and two openings 38 in Section 30. Openings 36 in section 28 are positioned to align with openings 38 in section 30 when the first and second body portion sections 28, 30 are folded upon each other along fold line 32. Closing film over the openings are provided by an adsorbent membrane 40 bonded to the body portion sections (FIG. 7). Thus, when folded, the openings and closing film form a pair of closed lens holding compartments 42 to maintain the lenses in relatively fixed positions.

Lens holding devices 26 like those illustrated in FIGS. 6 and 7 are formed by advancing a continuous strip of plastic material such as polystyrene having a width of approximately 2 ¼ inches along a preselected path of travel from a supply roll and simultaneously advancing an adhesive film of about 1⅞ inches width along that same path of travel from a supply roll to and against the plastic material. The two materials are bonded, and the result is thereafter directed to a cutting station where the circular openings 36, 38 are formed. The bonded and perforated material continues movement along the preselected path of travel where it is joined by a continuous strip of a protein binding membrane advancing along the same path of travel from a supply roll and against the adhesive film to adhere the protein binding material to the plastic material and form circular compartments as previously described. The bonded and perforated plastic material and adhesive film, with the attached protein binding material is then cut into discrete lengths to form individual holding devices such as shown in FIGS. 6 and 7. The bonded material is preferably creased or perforated to form fold line 32 prior to the cutting operation. Second body portion section 30 may also be cut along line 44 to form subsections so that one lens may be placed and closed before the second lens is engaged.

The strip of plastic material, such as polystyrene, may have a thickness of between 0.012 and 0.030 inch. Circular openings 36, 38 are preferably about 0.630 inch in diameter and, when folded, will create a cylinder compartment of that diameter with a compartmental thickness of from 0.024 to 0.060 inch. Since a conventional contact lens diameter is from 0.5 to 0.6 inch (12–15 mm), compartments 42 provide a snug enclosure for each lens.

The amount of current directed around the lens should be at the minimum possible consistent with adequate cleaning in order to avoid adverse consequences to the lens and to minimize the consumption of energy. To ensure the unidirectional flow of the charged contaminants, direct current should be applied. Direct current from a commercial 9 volt 300 milliamp A.C. adapter available from Radio Shack (Tandy Corporation), Dallas, Tex., is suitable. The preferred current level is less than 25 milliamps applied for 15 minutes or less. Higher current levels and longer times are possible but only add to the cost and little to the results.

A test procedure was developed to measure the DC resistance of various types of commonly used contact lenses that are suitable for being held and cleaned in accordance with the present inventive concept. One test was performed on the cleaning device and three tests were performed on lenses consumers might buy from an optician. The maker and lens type name are listed in the following table along with the data gathered for each lens type.

| No. | Mfg. | Lens Type | Unwashed Lens | Washed Lens | Dry Lens |
| --- | --- | --- | --- | --- | --- |
| 1. | Gentle Touch | Bifilcon | 50000 | 125000 | * |
| 2. | Gentle Touch | Neutrafilicon A | 40000 | 150000 | * |
| 3. | Bausch Lomb | Polymacon | 30000 | 125000 | * |
| 4. | Johnson Johnson | Etafilcon A | 13000 | 145000 | * |
| 5. | Bausch Lomb | Polymacon | 30000 | 120000 | * |
| 6. | Bausch Lomb | Polymacon | 25000 | 133000 | * |
| 7. | Bausch Lomb | Polymacon | 40000 | 300000 | * |
| 8. | Gentle Touch | Neutrafilcon | 12000 | 10000000 | * |
| 9. | Gentle Touch | Neutrafilcon | 16000 | 500000 | * |
| 10. | Johnson Johnson | Etafilcon A | 20000 | 100000 | * |
| 11. | Bausch Lomb | Polymacon | 20000 | 200000 | * |
| 12. | Bausch Lomb | Polymacon | 50000 | 400000 | * |

* Indicates a value greater than 500,000,000 ohms

In the first test, a representative commercial saline solution from Bausch & Lomb was placed in the cavity of the device with and without the lens holder. At current levels of 10 to 25 milliamperes achieved with voltages from 3.3 to 4.7 volts, the resistance of the saline solution was found to range from 180 to 360 ohms. Placing the lens holder in the device raised the resistance an insignificant amount. Thus, the fluid in this device under these low current levels is conductive.

Electrical testing of the lenses was conducted with a Hewlett-Packard 410B meter to measure the DC resistance. Tests were conducted at an ambient temperature of 75 degrees F. In the first test of the lenses, they were removed from their package containing saline solution and positioned on a holding fixture by seating the concave portion of each lens on the spherical element, thus sandwiching the lens between the holding surfaces of the test fixture. The data showing resistance values from 12,000 to 50,000 ohms indicate lenses soaked in saline solution exhibit a significant resistance to the flow of current through them. At 4.7 volts (a high voltage in the current cleaning device) against a resistance of 12,000 ohms, only 0.0004 amps of current would flow. Testing demonstrated the need for from 10 to 25 mA of current to achieve lens cleaning. At 12,000 ohms resistance, approximately 300 volts would be required to produce the 25 mA current flow. That voltage far exceeds the National Electrical Code requirements for safe operation of this type device.

In the second lens test, all conductive fluids associated with packaging or shipment were removed, and the lens to be tested was placed in a clean container with approximately 100 cc of distilled water. The lens was then agitated for a minimum of three minutes. After the wash, the lens was carefully removed by the use of latex gloves or finger cots, and the distilled water discarded. The washed lens was then placed on the holding fixture as noted above. The data indicates resistance levels from 100,000 to 1,000,000 ohms. This demonstrated that the saline solution in and around the lens is the electrical conductor.

In the third lens test, the washed lenses from test two were dried and placed upon the holding fixture as noted above. The resistance in all dried lenses exceeded 500,000,000 ohms. This is consistent with the fact that these lenses are made of plastic materials that are known electrical insulators.

It is apparent from these tests that the current path was through the saline solution and around, not through, the lens. The tests clearly demonstrate that none of the lenses were conductive and all functioned as insulators at the recommended and safe current levels. The conditions in the present cleaning device where less than 5 volts produces a current of 25 mA indicate a resistance of no more than 200 ohms within the device. The electrical flow path is therefore around and over the surface of, not through the lens.

It will be apparent to those skilled in the art that variations may be made in the components and methods of the present invention without departing from the spirit and scope of thereof. While components and methods in accordance with the invention have been specifically exemplified in the foregoing, it will be understood that the example is for the purpose of illustration and that modifications are contemplated. The invention is defined by the following claims with equivalents to the claims to be included therein.

What is claimed is:

1. A holding device for holding one or more contact lenses comprising: a body portion having a first body portion section and a second body portion section, the first and second body portion sections each having inside and outside surfaces and being integrally joined and foldable upon each other along a fold line; a device handling tab joined to a least one of the body portion sections; one of the openings in each of the body portion sections, the one or more openings in the first body portion section positioned to align with the one or more openings of the second body portion section and form one or more cylindrical openings to hold the one or more lens; substantially flat closing seals covering and closing each of the body portion section openings in the first body portion section wherein the closing seals and the openings in each body portion section form one or more closed lens holding compartments having substantially flat closing seal sides to maintain the one or more lens in a relatively fixed and substantially untouching position when the first and second body portion sections are folded upon each other along the fold line.

2. A lens holding device for holding a least two contact lenses comprising: a body portion having a first body portion section and a second body portion section, the first and second body portion sections having inside and outside surfaces and being integrally joined and foldable upon each other along a fold line; a device handling tab affixed to at least one of the body portion sections; a least two openings in each of the body portion sections, the openings in the first section positioned to align with the openings of the second section and form at least two cylindrical openings to hold the lens; substantially flat closing seals covering and closing each of the outside surface openings in the first body portion section and each of the outside surface openings in the second body portion section wherein the closing seals and the openings in each body portion section form closed lens holding compartments having substantially flat closing seal sides to maintain the lens in a relatively fixed and substantially untouching relationship with each other and the closing seals when the first and second body portion sections are folded upon each other along the fold line.

3. The device as claimed in claim 2 wherein the second body portion section is sectioned to form a plurality of second body portion subsections with each formed subsection having an opening therein and being foldable along the fold line to align with an opening in the first body portion section.

4. The device as claimed in claim 3 wherein the handling tab is integral with the first body portion section.

5. The device as claimed in claim 2 wherein the thickness of the first and second body portion sections is within the range of from 0.012 inch to 0.03 inch.

6. The device as claimed in claim 2 wherein the diameter of the first and second body portion section openings is about 0.63 inch.

7. Apparatus for supporting and moving contaminants from non-permeable contact lens comprising: a housing including a cleaning well; electrode means positioned within the cleaning well; lens holding means removably received by the cleaning well including a body portion having first and second integrally joined body portion sections foldable upon each other along a fold line, the first and second sections having openings therein which align with each other when the sections are folded, and substantially flat membranes to enclose and form lens holding compartments; one or more contact lens held by one or more of the lens holding compartments in a substantially untouching position; a power source for supplying electric current to the electrode means; adsorbent means disposed between the contact lens and the power source; control means for selectively directing current flow to the electrode means; and a predetermined quantity of cleaning solution held within the cleaning well immersing the electrode means, contact lens and adsorbent means completing an electric circuit so that upon actuation by the control means, current flow will pass from the power source through the electrode means, the cleaning solution, the adsorbent means and over the surface of the contact lens and back to the opposite electrode and then back to the power source so that contaminates accumulated on the contact lens migrate to the adsorbent.

8. The apparatus as claimed in claim 7 wherein the power source operates at 28 volts or less.

9. The apparatus as claimed in claim 8 wherein the cleaning well includes a substantially cylindrical chamber and opposed retaining slots formed within the chamber wall to removably receive the lens holding means.

10. A method of removing contaminants from a non-permeable contact lens having first and second surfaces comprising the steps of: positioning the contact lens, an adsorbent, and an electric current source so that the adsorbent is disposed between the contact lens and the electric current source; immersing the contact lens, the adsorbent, and the electric current source so disposed in a cleaning solution; and directing an electric current from the current source through the cleaning solution, the adsorbent, and solely over the surface of the contact lens so that contaminants carried by the contact lens migrate to the adsorbent.

11. The method as claimed in claim 10 wherein the electric current source flows at 28 volts or less.

12. A method according to claim 11 wherein the electric current flowing solely over the surface of the contact lens is less than 50 milliamperes.

13. Apparatus for removing contaminants from a non-permeable contact lens comprising: a housing including a cleaning well; electrode means positioned within the cleaning well; lens holding means removably received by the cleaning well; membrane means associated with the lens holding means; one or more contact lenses held by the lens holding means in a substantially untouching relationship with the membrane means; a power source for supplying electric current to the electrode means; adsorbent means within the lens holding means disposed between the contact lens and the power source; control means for selectively directing current flow to the electrode means; and a predetermined quantity of cleaning solution held within the cleaning well immersing the electrode means, contact lens and adsorbent means completing an electric circuit so than upon actuation by the control means, current flow will pass from the power source through the electrode means, the cleaning solution, the adsorbent means and over the surface of the contact lens and back to the opposite electrode and then back to the power source so that contaminants accumulated on the contact lens migrate to the adsorbent.

14. The apparatus as claimed in claim 13 wherein the power source operates at 28 volts or less.

15. The apparatus as claimed in claim 14 wherein the current is less than 50 milliamperes.

16. The apparatus as claimed in claim 15 wherein the control means includes a power actuating means and an indicator for circuit continuity.

17. The apparatus as claimed in claim 16 wherein the cleaning well includes a substantially cylindrical chamber having a floor and wall and opposed retaining slots formed within the chamber wall to removably receive the lens supporting means.

18. The apparatus as claimed in claim 17 wherein the electrode means are extended wire elements having a length within the range of from 5 millimeters to 60 millimeters.

19. The apparatus as claimed in claim 18 wherein the power source is one or more batteries.

20. The apparatus as claimed in claim 19 wherein the power source is a converter for utilizing an alternating current power source.

21. An apparatus for supporting and removing contaminants from non-permeable contact lens comprising: a housing including a cleaning well; electrode means positioned within the cleaning well; lens holding means removably received by the cleaning and including a body portion having a first body portion section and a second body portion section, the first and second body portion sections having inside and outside surfaces and being integrally joined and foldable upon each other on the fold line; a device handling tab affixed to at least one of the body portions, at least two openings in each of the body portion sections, the opening in the first section positioned to align with the opening of the second section and form at least two cylindrical openings to hold the lens, closing seals covering and closing each of the outside surface openings in the first body portion section and each of the outside surface openings in the second body portion section wherein the closing seals and the openings in each body portion section formed closed lens holding compartments to maintain the lens in a relatively fixed relationship with each other when the first and second body portions are folded upon each other along the fold line; one or more contact lens held by; a power source for supplying the electric current to the electrode means; one or more contact lenses held by one or more of the lens holding compartments such that the closing seal is disposed between the contact lens and the power source; control means for selectively directing current flow to the electrode means; and a predetermined quantity of cleaning solution held within the cleaning well and contiguous with the electrode means, contact lens and closing seal completing an electric circuit so that upon actuation by the control means, current flow will pass from the power source through an electrode means, the cleaning solution, the closing seal and over the surface of the contact lens and back to the opposite electrode and then back to the power source.

22. The apparatus as claimed in claim 21 wherein the power source operates at 28 volts or less.

23. The apparatus as claimed in claim 22 wherein the cleaning well includes a substantially cylindrical chamber having a floor and wall and opposed retaining salts formed within the chamber wall to removably receive the lean holding means.

\* \* \* \* \*